United States Patent
Smith-McCune et al.

(10) Patent No.: US 6,221,623 B1
(45) Date of Patent: Apr. 24, 2001

(54) BIOCHEMICAL METHODS FOR DETECTING CERVICAL DYSPLASIA AND CANCER

(75) Inventors: Karen Smith-McCune, San Francisco; Ellen Beth Grossnickle, San Diego; Nooshin Razani, San Francisco, all of CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/189,124

(22) Filed: Nov. 10, 1998

Related U.S. Application Data

(60) Provisional application No. 60/065,206, filed on Nov. 10, 1997.

(51) Int. Cl.⁷ .............................. G01N 33/53; C12Q 1/68
(52) U.S. Cl. .............................. 435/7.23; 435/6; 435/7.1; 435/40.5; 435/40.51; 435/40.52; 435/68.1; 436/503; 436/535; 436/43; 530/387.1
(58) Field of Search ................................. 435/6, 7.23, 7.1, 435/40.5, 40.51, 40.52, 68.1; 436/503, 535, 43; 530/387.1

(56) References Cited

PUBLICATIONS

Garzetti et al. Microinvasive Cervical Carcinoma and Cervical Intraepithelial Neoplasia; Biologic Significance and Clinical Implications of 72–kDa Metalloproteinase Immunostaining. May 1996, vol. 61, No. 2, pp. 197–203, whole document.

*Primary Examiner*—Geetha P. Bansal
(74) *Attorney, Agent, or Firm*—Richard Aron Osman

(57) ABSTRACT

Primary screening for cervical dysplasia is effected by measuring a biochemical marker of apoptosis and/or angiogenesis in each of a population of cells derived from convenient, superficial swabbing, sponging, scraping or lavage of superficial epithelial cells from the cervix, wherein the marker indicates the presence of cervical dysplasia in the sample, and scoring the results of the measuring step for cervical dysplasia (i.e. ascertaining whether or not the marker is present) in the patient in the absence of any cytological examination.

23 Claims, No Drawings

US 6,221,623 B1

BIOCHEMICAL METHODS FOR DETECTING CERVICAL DYSPLASIA AND CANCER

This application claims benefit to U.S. Provisional application Ser. No. 60/065,206 filed Nov. 10, 1997.

FIELD OF THE INVENTION

The field of the invention is biochemical methods for screening for cervical dysplasia and cancer in exfoliated cells.

BACKGROUND OF THE INVENTION

Human cervical epithelium can elaborate a series of progressive neoplastic changes known as cervical dysplasia or cervical intraepithelial neoplasia (CIN), which are precursors to invasive cervical cancer. The designations CIN I, II and III refer to mild, moderate, and severe dysplasia/carcinoma in situ, respectively. This histological grading scheme is based largely on the extent to which the thickness of the epithelium is replaced by mitotically active cells with enlarged, hyperchromatic nuclei [1]. Untreated, a subset of dysplastic lesions will advance to cancer, with a frequency that increases dramatically in CIN III lesions [2]. Infection with the human papillomavirus (HPV) is strongly correlated with the development of cervical cancer [3, 4]. HPV is present in over 90% of CIN lesions [5], 95% of cervical cancer [4], and 93% percent of anal squamous cancers in women [6].

In many developing countries, cervical cancer is the most common cancer (excluding skin) in women and the major cause of cancer-related deaths in women [7]. In the United States, abnormalities on Papanicolaou, or "Pap" smears are detected in millions of women annually, resulting in an estimated annual cost of $6 billion for patient evaluation and treatment [8]. The success of Pap smear screening is reflected by the fact that there are only approximately 15,000 new cases of cervical cancer annually in the United States. Indeed, a significant body of evidence supports the observation that population-based Pap smear screening can significantly reduce the incidence of cervical cancer between 3 and 10-fold [9]. Nevertheless, at least 10% of dysplasia cases are diagnosed as negative by Pap smear (false negative).

The Pap smear test consists of collecting cells from the cervix and vagina, spreading them onto a glass slide, fixing and staining the cells, and analyzing them under a microscope. Cytological features that distinguish dysplastic cells, such as enlarged hyperchromatic nuclei and increased nuclear/cytoplasmic ratio, are identified by visually scanning the entire slide. While the success of the Pap smear at detecting cervical precancers and cancers is irrefutable, the assay has several limitations: It is a sampling technique in which typically fewer than half of the cells collected from the cervix are transferred to the slide for analysis, contributing to false negative test results. It is dependent upon human observers to read each cell on the slide, generating another source of false negative results due to observer error. It has a relatively long turn-around time, ranging from several days to weeks, impeding effective followup in much of the world. The test is relatively labor-intensive and requires trained personnel, making it unavailable as a screening test in many areas. Some of these limitations have recently been addressed by new technologies available in North America and Europe. Cytyc Corp has introduced an improved collection and slide preparation technique called the ThinPrep Test in which cells are collected into a liquid fixative rather than directly applied to a slide in the field, and delivery of the cells to the slide is performed mechanically, generating a random distribution of cells on the slide more representative of the original population of cells collected. The slides generated by this technology are easier to interpret microscopically, making the test more sensitive to abnormalities. Two companies have recently marketed computers based on neural network programming which digitally analyze cells on Pap smears and identify cells suspicious for dysplasia and cancer: these cells are then reinterpreted by a human observer. This technology is intended to reduce the false negative rate, and is currently only recommended for slides that have previously been analyzed in the conventional fashion and read out as negative.

Similarly, other attempts to identify noncytological markers of cervical dysplasia have only confirmed the need to supplement such assays with conventional cytological examination such as Pap smear to effect clinical diagnosis with tolerable accuracy, e.g. Kyo S et al. (1997) Application of telomerase assay for the screening of cervical lesions. Cancer Res 57(10), 1863–1867; Pillai MR (1996) The presence of human papillomavirus-16/-18 E6, p53, and Bcl-2 protein in cervicovaginal smears from patients with invasive cervical cancer. Cancer Epidemiol Biomarkers Prev 5(5), 329–335. Accordingly, an object of the invention is to provide a screening method amenable to wider, preferably ready, international availability, that can detect premalignant cervical disease before it becomes invasive without the need for any supplemental conventional cytological examination.

SUMMARY OF THE INVENTION

The invention provides methods and compositions for primary screening for cervical dysplasia. The methods involve measuring a biochemical marker in each of a population of cells derived from convenient, superficial swabbing, sponging, scraping or lavage of superficial epithelial cells from the cervix, wherein the marker indicates the presence of cervical dysplasia in the sample, and scoring the results of the measuring step for cervical dysplasia (i.e. ascertaining whether or not the marker is present) in the patient in the absence of any cytological examination. The methods obviate the need for any cytological examination, providing a primary diagnostic clinical screen without the need for time, labor and material intensive resources such as microscopy equipment, etc. The marker or diagnostic marker threshold is present/exceeded in at least 65%, preferably at least 75%, more preferably at least 85% of high grade dysplasia cases.

Accordingly, the invention provides means to detect precancerous or cancerous conditions of the cervix by a label (e.g. fluorescent or colorimetic) that is amenable to low-technology analysis and/or automated, machine-readable analysis. The invention includes the surprising finding that a high proportion of cells containing biochemical markers of dysplasia can be detected in superficial cervical epithelial cells (e.g. scrapings, lavage samples, swabs, etc.) from women with precancerous cervical dysplasia, avoiding the need for any cytological examination.

In one embodiment, the marker is a marker which portends apoptosis, such as markers of DNA fragmentation, caspase activity, membrane lipid distribution, subdiploid DNA content, etc. In another embodiment, the marker is a marker of angiogenesis, such as an endothelial cell-specific surface protein, secretory protein, growth factor, etc., angiogenic ephrin (Gibaldi M *J Clin Pharmacol* 1998 Oct;38(10) :898–903), angiogenic matrix metalloproteinases (Sang QX *Cell Res* 1998 Sep;8(3):171–7), etc. Essentially the presence in superficial cervical epithelial cells of any biochemical marker, particularly markers of apoptosis and angiogenesis, the presence of which in subsuperficial cervical epithelium is correlated with dysplasia can be used in the invention.

In one embodiment of the invention, cells from a cervical scraping or lavage are suspended in a buffer solution containing digestive enzymes and mixed well. The resulting tissue and cells suspension is stained with a kit containing terminal deoxytransferase, fluorescent-labeled nucleotide and other reagents necessary for cell permeability, high labeling efficiency and low non-specific staining. The cells are scored for nuclear and cytoplasmic staining by either microscopic examination or laser flow cytometry. Dysplasia is diagnosed by the staining index after correction for non-epithelial cell staining.

DETAILED DESCRIPTION OF PREFERRED EMBODIMENTS

The following descriptions of preferred embodiments are offered by way of illustration and not by way of limitation:

It is disclosed herein that cervical dysplasia and cancer contain unique cellular and molecular properties which distinguish them from normal tissue and that these properties can be detected in superficial and exfoliated cervical epithelial cells. Accordingly, the invention adapts these molecular characteristics that are unique to dysplasia for rapid, simple, on-site diagnosis of cervical cancer and its precursors; screening which is not currently available to the majority of women worldwide due to the cost and expertise required for conventional Pap smear screening. The invention provides rapid, inexpensive and reliable assays that can be delivered at the point of care and used as the basis for immediate triage for women requiring further evaluation. The assays are as simple as a dipstick performed in lysed cervical cells, in which a chemical reaction (e.g. a colorimetric enzyme assay, such as ELISA) generates a color indicating the presence of dysplasia or cancer, indicating the need for further evaluation at the time of the patient's initial visit. For example, a color-generating marker-detection reagent (e.g. antibody, substrate, etc.) may be incorporated into or on a probe for sampling exfoliated cervical epithelial cells in or removed from the vagina. In a particular application, the reagent is impregnated into tampon-like probes.

The invention defines two seminal events in tumor progression, angiogenesis and apoptosis, which distinguish normal cervical epithelium from neoplastic cervical disease. In a particular embodiment, the invention compares the biochemical properties of dysplastic and malignant cervical cells to normal cells by measuring other markers of apoptosis including caspase activity, membrane lipid distribution, subdiploid DNA content on flow cytometry, etc., maximizing assay sensitivity, specificity, reproducibility, and reliability in clinical samples.

In another particular embodiment, the invention measures biochemical changes that portend or are associated with the appearance of new blood vessels, or angiogenesis, in association with the appearance of cervical dysplasia. Angiogenesis underlies the colposcopic detection of cervical cancer; the appearance of atypical vessels within dysplastic epithelium is strongly correlated with microinvasive and invasive cancer [10]. Colposcopic vascular patterns of punctation and mosaicism are evidence of premalignant changes, and have been attributed to remodeling of the existing vascular network by the presence of CIN [11]. The molecular basis of angiogenesis in the cervix and the factors mediating this event, however, have not been hitherto defined.

A correlation of angiogenic markers with cervical disease was initially demonstrated using immunohistochemical staining for von Willebrand factor (vWf), a marker of endothelial cells. The results demonstrated a dense network of microcapillaries in the subepithelial stroma immediately below dysplastic epithelium, with a statistically significant increase in number of microvessels associated with high grade CIN lesions compared to low grade lesions and benign cervix [12–15]. In situ hybridization of lesions for a common tumor angiogenic factor, vascular endothelial growth factor/vascular permeability factor (VEGF/VPF), has demonstrated progressive upregulation of expression of this factor in dysplastic epithelium, implicating VEGF/VPF as a possible mediator of the angiogenic phenotype of dysplastic lesions [12, 14]. In addition, the angiogenic properties of histologically benign cervical mucosa are altered in the presence of nearby dysplastic lesions, indicating that angiogenesis is a more sensitive marker than histology for the presence of adjacent CIN [16].

Recently, a transgenic mouse model of progressive squamous carcinogenesis has been developed in which the expression of HPV oncogenes E6 and E7 was targeted to the basal cell layer under regulation of the keratin 14 promoter [17,18–20]. Comparison of the angiogenic properties and VEGF/VPF expression of progressive lesions in this model to human cervical lesions demonstrated remarkable parallels [12]. Furthermore, treatment of the animals with estrogen results in the development of cervical squamous cancer precursors and invasive lesions, providing an animal model for HPV-induced genital cancer [21]. These transgenic animals are useful for determining the effect of angiogenesis on the natural history of neoplastic squamous lesions and demonstrating the efficacy of candidate inhibitors of angiogenesis to arrest the development of invasive cancer.

As discussed above, there is a strong association between HPV and cervical cancer. This correlation has spurred interest in the use of HPV detection as an adjunct to cervical cancer detection. However, HPV testing has not generated a reliable clinical assay for dysplasia due to the high prevalence of asymptomatic HPV infection [22, 23]. One of our strategies has been to identify intracellular events that are initiated by HPV infection in order to identify key indicators that herald the development of cervical neoplasia. The molecular basis of the association of HPV with cervical cancer is attributed to the properties of the E6 and E7 oncoproteins encoded in the early region of the viral genome [24]. Both of these genes have important effects on the cell cycle by binding to and inactivating tumor suppressor genes. E6 results in ubiquination and degradation of the tumor suppresser gene p53 [25, 26]. E7 binds to the retinoblastoma gene product, pRb [27], and is postulated to exert its transforming effect by releasing an active form of the transcription factor E2F from its association with pRb. We have focused on the downstream events following E7 activation. Using an inducible epitope-tagged chimera of HPV16 E7, we have compared the intracellular binding of E7 to the Rb-family members pRb, p107 and p130. This work has yielded the surprising result that p130, rather than pRb itself, is the preferred intracellular partner of E7, indicating a novel role for E7 in regulating the transition from $G_0$ to $G_1$ in the cell cycle. We use the inducible allele to identify E7 transcriptional target genes by differential display, comparing mRNA populations in cells in which E7 is active versus those in which it is inactive. These experiments have identified a population of mRNA gene products that are induced upon E7 activation, and surprisingly, an equal number of rnRNAs that are repressed by E7.

Another aspect of E7 function is the ability of E7 to induce programmed cell death, known as apoptosis. We have used the inducible E7 chimera to show that E7 can induce apoptosis in starved cells: upon activation of E7, there is a 3–10 fold induction of apoptosis. Overexpression of bc1-2, a known inhibitor of apoptosis, completely blocks the induction of apoptosis by E7, indicating that the apopototic pathway induced in these cells occurs through standard pathways. Overexpression of HPV 16 E6, which binds to p53 and results in decreased levels of p53 through ubiquination, does not block E7 -induced apoptosis, indicating that E7 -induced apoptosis occurs through a p53 -independent pathway.

As a result of these observations, we hypothesized that apoptosis induced by E7 might be important in the disease process caused by HPV; we therefore undertook to study apoptosis in dysplasia and cancer from human cervical biopsies. Using a histochemical method for detecting fragmented DNA, a marker for apoptosis, we have found that DNA fragmentation is a rare event in normal cervix from patients undergoing hysterectomy for benign disease: in a total of 7 samples studied, 3 had minimal to no DNA fragmentation in the superficial cell layers, and the remaining 4 had small areas of signal corresponding to 15% of the total epithelial length. Conversely, in dysplastic tissue, the superficial layers (distal from the basal cells) contained numerous cells with fragmented DNA that nevertheless did not exhibit morphological features of apoptosis. This observation is true in 13 of 14 samples of high grade dysplasia. The one sample of high grade dysplasia that did not show this phenotype was a cervical punch biopsy, whereas the rest of the samples were derived from loop and cone biopsies, which are much larger samples and therefore possibly less subject to mechanical artifact. The depth of staining in the superficial cell layers varied between one and seven cells deep in different samples. The histological boundary between normal cervical mucosa and dysplastic epithelium was marked by an abrupt transition between minimal staining (normal) to marked staining in the upper layers (dysplasia). Seven samples of invasive cervical cancer specimens also demonstrated DNA fragmentation in the superficial cell layers, although in some samples the phenotype was not as pronounced as that in dysplasia. Low grade lesions had variable staining compared to high grade lesions; of 6 low grade samples studied, 2 demonstrated no staining (25%), 2 demonstrated a similar pattern to the dysplastic tissue described above, and 2 demonstrated a discrete layer of apoptosis in the middle epithelial layers, and minimal staining in the superficial layers.

Other investigators have studied the staining of cervical samples with a similar staining technique for detecting the free ends of DNA [29–32]. In 2 reports, the measured % of apoptotic cells increased during the progression from normal to cervical cancer [30, 32], and in two cases the % of apoptosis decreased [29, 31]. In all studies, the authors determined the apoptotic index by analyzing cells that not only stained positive for DNA fragmentation, but also had morphological features of apoptosis such as nuclear fragmentation; therefore, they did not include the cells in the superficial layers described above in their analyzes. The samples used in their studies were cervical biopsy specimens, which in our experience were not as sensitive at detecting the presence of superficial cells exhibiting DNA fragmentation as were the larger loop and cone biopsy samples. Therefore we conclude that the appearance of DNA fragmentation in the superficial layers of cervical neoplasia represents a novel phenotype previously unrecognized and specific to cervical dysplasia and cancer.

We have also found that apoptotic cells can be detected in exfoliated cells from patients with high grade dysplasia. Indeed, the presence of apoptotic cells is strongly correlated with the presence of dysplasia in samples collected for Pap smears: whereas samples from patients with normal cytology contained a low percentage of cells with fragmented DNA [mean 2.3%, range 0–8.5%,N=7], samples from women with cytology showing high grade dysplasia contained significant proportions [mean 17%, range 1–31%, N=7], as did samples showing low grade dysplasia [mean 18.3%, range 0.5–45%, N=7]. In addition, many of the cells which stain positive for DNA fragmentation contain morphological features of apoptosis such as fragmented nuclei. These data indicate that apoptosis (as determined by DNA fragmentation) can be measured in samples collected for conventional cytological analysis by Pap staining, and appears to be a sensitive and specific marker of high grade dysplasia.

The results described above demonstrate that apoptosis, as measured by DNA fragmentation, is upregulated in dysplastic tissues. Many additional biochemical processes are initiated when cells undergo apoptosis and we show that these processes are present in dysplastic epithelium, confirming that the DNA fragmentation present in dysplastic epithelium reflects apoptosis, and providing other biochemical markers of dysplasia which are adaptable to a solid substrate-based assay. Samples for analysis are performed as follows: cervical cells are collected from women during performance of Pap smears for routine indications. After collection of a subpopulation of these cells on glass slides, as is usually done clinically, the remaining cells are collected from the spatula by agitation in physiological saline. The cells are either delivered for immediate use, or pelleted by centrifugation and the pellets stored at $-70°$ C. Another source of cells is available in ThinPrep material, since only approximately 10% of the cells are used to prepare the cytologic slide, and the rest are available for analysis as methanol-fixed samples. These cells are analyzed from the appropriate source as described below, and the results correlated to the cytological diagnosis.

Morphology by electron microscopy: One of the distinguishing features of apoptosis is that cell death occurs through a set of morphological changes that are distinct from necrosis. These features have been well-characterized by electron microscopy. Therefore, we fix and stain exfoliated cervical tissues for electron microscopy, validating that the DNA fragmentation measured in these samples as described above indeed reflects the process of apoptosis. Samples are examined for chromatin condensation, cytoplasmic vacuolization, and nuclear fragmentation.

Caspase activity: The destruction of a cell undergoing apoptosis is accomplished by a family of proteases with unique biochemical properties. This family of proteases is termed caspases to refer to the enzymatically active amino acid being a cysteine molecule (caspase), and cleavage occurring after aspartic acid (cease). The family thus far has 10 members [33]. In cells induced to undergo apoptosis, caspases are activated by proteolytic cleavage by upstream proteases or by autocatalysis. Caspase activity can be assayed enzymatically with fluorogenic substrates which are available commercially. They can also be detected by Western blotting with commercially available antibodies to detect proteolytically-derived breakdown products, reflecting activation of enzymatic activity. A third technique for analyzing caspase activity is to measure the breakdown products of the physiological substrates, such as PARP, on Western blots of cells lysates. Each of these techniques can be readily performed on lysates of cervical cell samples collected for conventional cytological analysis. Samples are resuspended in lysis buffer, an aliquot removed for protein determination, and aliquots containing a standardized amount of protein analyzed in parallel for enzymatic activity and by Western blotting. Western blots are analyzed both for the presence of caspase breakdown products (indicating enzymatic activity) and PARP catalysis. We find that the detection of enzymatic caspase activity is prognostic of apoptosis in these cells.

Annexin V: Apoptosis results in an inversion of phosphatidyl serine from the inner to the outer leaflet of the lipid bilayer [34]. Phosphatidyl serine can then be measured by its ability to bind the anticoagulant annexin V. These assays require unfixed cells. Therefore, after collection in clinic, samples are rinsed with culture medium and then incubated directly with FITC-conjugated annexin V. The amount of binding per cell is analyzed by flow cytometry. Alternatively, the fluorescent binding of identical numbers of cells is measured and compared as a function of cytological diagnosis.

Measurement of DNA fragmentation. Several techniques exist for measuring the breakdown products resulting from intranuclear DNase activity. For example, DNA preparations can be resolved on agarose gel electrophoresis and examined for the presence of laddering. Alternatively, cells can individually analyzed for DNA damage in the comet assay of the single cell gel assay [35]. These techniques are performed on clinical samples and analyzed to determine the correlation between DNA fragmentation and cytological diagnosis.

Subdiploid DNA content on flow cytometry: Another feature of apoptosis useful as a diagnostic marker is that apoptotic nuclei fragment and hence contain subdiploid quantities of DNA. Therefore, nuclear preparations having subdiploid quantities of DNA are pathognomonic of apoptosis. Cells are collected from patients in Gynecology clinic and Dysplasia Clinic as described above, lysed in nonionic detergent, and the nuclei collected and stained with a fluorescent DNA dye such acridine orange. Nuclei are analyzed by flow cytometry, with primary human fibroblasts being used as a control for normal diploid chromosome number. The percent of nuclei with subdiploid DNA content is measured in each sample and compared to the cytological diagnosis.

Measurement of cytoplasmic histone content: As a result of DNA fragmentation, nucleosomes are released from the nucleus into the cytoplasm, providing the basis for another assay for apoptosis. An ELISA-based assay is commercially available for measurement of histones in this purpose, with the detection consisting of a colorimetrically-based assay for histones in nuclear-free cell lysates.

The above experiments provide a set of markers of apoptosis which can be measured in exfoliated cervical cell samples. These markers are validated in a pilot assay for use in clinical settings. Preferred assay criteria for a useful assay are 1) that it give reliably consistent results under varying conditions, 2) that it require equipment that is widely available or easily obtainable and maintained, 3) that it can be performed by personnel with limited technical training, and 4) that it be comprised of relatively stable materials. The specificity of apoptosis as a marker for cervical neoplasia in different populations, including adolescent and postmenopausal women and women with concurrent sexually transmitted diseases or inflammation, etc. is also confirmed. Hence, we use these criteria to evaluate the available methods for detecting biochemical markers that distinguish dysplastic cells from normal. We select the marker and associated method of detection that fulfills the above criteria to the greatest extent and develop that test for widespread testing. Central to this aim is the desire to not only identify a marker for dysplastic cells, but to further validate one that can be detected and measured in the broadest clinical context. Accordingly, technologies developed in such industries as food quality and environmental monitoring, appropriate health technology, medical field use technology, and home health monitoring provide basic assay technologies that have proven stable enough for widespread field application. Clinical samples are collected and analyzed in a prototypic fashion to confirm sensitivity, specificity, reproducibility, and reliability of lead assays.

Parallel strategies are employed to enumerate other molecular differences between normal and neoplastic cervical tissue. One such strategy consists of a high throughput screen for detecting MnRNA transcripts unique to neoplastic tissue. A technique for expression monitoring by hybridizing cDNA to high-density oligonucleotide arrays [36] is applied to monitor genes whose expression is restricted to dysplasia and is absent in normal cervix. The analyzes are performed as follows: Samples of cervical cells are collected from women at the time of Pap smears performed in Gynecology Clinic and Dysplasia Clinic as described above, and cell pellets stored at −80° C. After the cytological diagnosis has been determined in the clinical labs, RNA are prepared from samples demonstrating normal cytology, as well as those demonstrating high grade dysplasia. Each collection contains 250,000–500,000 cells which yields approximately 5–10 ug of total RNA (based on an average yield of 20 ug of RNA per 106 cells in our lab). Since the cells in the uppermost layers of squamous epithelium (those sampled by exfoliative cytology) are highly differentiated, we the yield of MRNA from these cells is slightly less that the 10% of total RNA normally present in proliferating cells, and may even be as low as 1% of total RNA. Therefore sample yields can vary 0.05 to 1 ug of mRNA. An appropriate number of samples of normal or high grade histology is pooled to generate 2 ug of mRNA for each analysis. The mRNA samples are then processed per Affymetrix protocol for hybridization to a Human Expression Chip Set. The pattern of MRNA binding to the chips from normal cervical cells is compared to that from high grade dysplasia. The data output identifies any transcripts that are consistently unique to the samples of high grade dysplasia.

Gene expression unique to cervical neoplasia using the Affymetrix technology is correlated with disease phenotype by in situ hybridization in a large number of tissue biopsy samples from patients with HPV disease as well as normal cervix. Diagnostic transcripts are also analyzed for their functional properties by overexpressing them in an antisense orientation in cancer cell lines to inhibit function of the endogenous transcripts, role cell cycle regulation and prognostic significance of gain or loss of expression of these transcripts in a natural history cohort of low-grade lesions.

REFERENCES

1. Ferenczy A Winkler B. Cervical Intraepithelial Neoplasia and Condyloma. In R. J. Kurman, Editor. Blaustein's Pathology of the Female Genital Tract, ; Springer-Verlag, 1987.
2. Ostor AG: *Int. J Gynecol. Path.* 1993;12:186–192.

3. Mukhopadhyay D, Tsiokas L, Zhou XM, et al.: *Nature* 1995;375:577–81.
4. Bosch FX, Manos MM, Munoz N, et al.:. *J Natl Cancer Inst* 1995;87:796–802.
5. Lorincz AT, Reid R, Jensen AB, et al.: *Obstet Gynecol* 1992;79:328–337.
6. Frisch M, Grimelius B, van den Brule A, et al.: *Abstract, 16th International Papillomavirus Conference, and in press, New Engl. J Med.*
7. Parkin D, Pisani P Ferlay J:. *Int J Cancer* 1993;54:594–606.
8. Kurman R, Henson D, Herbst A, Noller K Schiffinan M: *JAMA* 1994;271:1866–9.
9. Eddy D: Screening for cervical cancer. *Annals Int Med* 1990;113:214–226.
10. Sillnan F, Boyce J Fruchter R: *Am J Obstet Gynecol* 1981;139:154–159.
11. Stafl A Mattingly RF: *Am J Obstet Gynecol* 1975;121:845–851.
12. Smith-McCune K, Zhu Y-H, Hanahan D Arbeit J: *Cancer Res* 1997;57:1294–1300.
13. Smith-McCune K Weidner N: *Cancer Res* 1994;54:800–804.
14. Guidi A, Abu-Jawdeh G, Berse B, et al.: *J Natl Cancer Inst* 1995;87:1237–45.
15. Hanahan D Folkman J: *Cell* 1996;86:353–364.
16. Smith-McCune K, Zhu Y Darragh T: submitted 1997;
17. Arbeit JM, Munger K, Howley PM Hanahan D: *J Virol.* 1994;68:4358–68.
18. Arbeit JM: *Cancer Surveys* 1996;26:7–34.
19. Coussens LM, Hanahan D Arbeit JM: *Am J Pathol* 1996;149:1899–1917.
20. Hurlin PJ, Foley KP, Ayer DE, et al.: *Oncogene* 1995;11:2487–2501.
21. Arbeit JM, Howley PM Hanahan D: *Proc Natl Acad Sci USA* 1996;93:2930–5.
22. Bauer HM, Hildesheim A, Schiffinan MH, et al.: *Sex Transm Dis* 1993;20:274–8.
23. Wheeler CM, Parmenter CA, Hunt WC, et al.: *Sex Transm Dis* 1993;20:286–9.
24. zur Hausen H: *Virol.* 1991;184:9–13.
25. Wemess BA, Levine AJ Howley PM: *Science* 1990;248:76–9.
26. Scheffner M, et al.: *Cell* 1990;63:1129–36.
27. Dyson N, Howley PM, Munger K Harlow E: *Science* 1989;243:934–7.
28. Smith-McCune K, et al.: Intracellular localization and differential binding to Rb family members contribute to HPV16 E7 transformation capability. submitted 1997;
29. Furuya H, Yabushita H, Noguchi M Nakanishi M: *Nippon Rinsho* 1996;54:1916–21.
30. Isacson C, Kessis TD, Hedrick L Cho KR: *Cancer Res* 1996;56:669–74.
31. Sheets E, Crum C Yeh J: *Gynecol Oncol* 1996;63:94–100.
32. Shoji Y, Saegusa M, Takano Y, Ohbu M Okayasu I: *J Clin Path* 1996;49:134–138.
33. Martins L Eamshaw W: *Trends in Cell Biol* 1997;7:111–114.
34. Fadok V, Voelker D, Campbell P, et al.: *J Immunol* 1992;148:227.
35. Fairbairn D, Olive P O'Neill K. *Mutation Res* 1995;339:37–59.
36. Lockhart D et al: *Nature Biotech* 1996;14:1675–80.
37. Palefsky JM: *AIDS* 1994;8:283–295.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of primary screening for cervical dysplasia, said method comprising the steps of:
   measuring a biochemical marker of at least one of apoptosis and angiogenesis in each cell of a population of superficial epithelial cervical cells of a patient wherein the marker indicates the presence of cervical dysplasia in the patient; and
   scoring the results of the measuring step for cervical dysplasia in the patient in the absence of any cytological examination, wherein a supranormal amount of the biochemical marker relative to that present in non-dysplastic superficial epithelial cells provides a primary indicia of cervical dysplasia.

2. A method according to claim 1, wherein the marker provides an indicia of DNA degradation or fragmentation, caspase activity, membrane lipid distribution or subdiploid DNA content.

3. A method according to claim 1, wherein the marker provides an indicia of a von Willebrand factor (vWf), an angiopoieten, a vascular endothelial growth factor/vascular permeability factor (VEGF/VPF), an angiogenic ephrin or an angiogenic matrix metalloproteinase.

4. A method according to claim 1, wherein measuring step comprises a solid-phase immunoassay comprising reacting the marker with a marker-specific antibody and the scoring step comprises calorimetrically detecting the presence of complexes of the marker and the antibody.

5. A method according to claim 1, wherein the marker provides an indicia of DNA degradation or fragmentation.

6. A method according to claim 1, wherein the marker provides an indicia of caspase activity.

7. A method according to claim 1, wherein the maker provides an indicia of membrane lipid distribution.

8. A method according to claim 1, wherein the marker provides an indicia of subdiploid DNA content.

9. A method according to claim 1, wherein the marker provides an indicia of a von Willebrand factor (vWf).

10. A method according to claim 1, wherein the marker provides an indicia of an angiopoieten.

11. A method according to claim 1, wherein the marker provides a vascular endothelial growth factor/vascular permeability factor (VEGFNYPF).

12. A method according to claim 1, wherein the marker provides an indicia of an angiogenic ephrin.

13. A method according to claim 1, wherein the marker provides an indicia of an angiogenic matrix metalloproteinase.

14. A method according to claim 5, wherein measuring step comprises a solid-phase immunoassay comprising reacting the marker with a marker-specific antibody and the scoring step comprises colorimetrically detecting the presence of complexes of the marker and the antibody.

15. A method according to claim 6, wherein measuring step comprises a solid-phase immunoassay comprising reacting the marker with a marker-specific antibody and the scoring step comprises colormetrically detecting the presence of complexes of the marker and the antibody.

16. A method according to claim 7, wherein measuring step comprises a solid-phase immunoassay comprising reacting the marker with a marker-specific antibody and the scoring step comprises calorimetrically detecting the presence of complexes of the marker and the antibody.

17. A method according to claim 8, wherein measuring step comprises a solid-phase inmmunoassay comprising reacting the marker with a marker-specific antibody and the scoring step comprises colorimetrically detecting the presence of complexes of the marker and the antibody.

18. A method according to claim 9, wherein measuring step comprises a solid-phase immunoassay comprising reacting the marker with a marker-specific antibody and the scoring step comprises colorimetrically detecting the presence of complexes of the marker and the antibody.

19. A method according to claim 10, wherein measuring step comprises a solid-phase immunoassay comprising reacting the marker with a marker-specific antibody and the scoring step comprises colorimetrically detecting the presence of complexes of the marker and the antibody.

20. A method according to claim 11, wherein measuring step comprises a solid-phase immunoassay comprising reacting the marker with a marker-specific antibody and the scoring step comprises colorimetrically detecting the presence of complexes of the marker and the antibody.

21. A method according to claim 12, wherein measuring step comprises a solid-phase immunoassay comprising reacting the marker with a marker-specific antibody and the scoring step comprises colorimetrically detecting the presence of complexes of the marker and the antibody.

22. A method according to claim 13, wherein measuring step comprises a solid-phase immunoassay comprising reacting the marker with a marker-specific antibody and the scoring step comprises colorimetrically detecting the presence of complexes of the marker and the antibody.

23. A method according to claim 1, wherein the cells are obtained from a cervical scraping or lavage, are suspended in a buffer solution containing digestive enzymes and mixed well, stained with a kit containing a terminal deoxytransferase and a fluorescent-labeled nucleotide and scored for nuclear and cytoplasmic staining by either microscopic examination or laser flow cytometry, wherein dysplasia is diagnosed by a staining index after correction for nonepithelial cell staining.

* * * * *